United States Patent [19]

Roth et al.

[11] Patent Number: 4,708,776
[45] Date of Patent: Nov. 24, 1987

[54] SODIUM ION SELECTIVE ELECTRODE AND METHOD OF USE

[75] Inventors: Joseph A. Roth, Webster; Thomas A. Smith, Rochester, both of N.Y.

[73] Assignee: Eastman Kodak Company, Rochester, N.Y.

[21] Appl. No.: 890,060

[22] Filed: Jul. 28, 1986

[51] Int. Cl.⁴ .......................................... G01N 27/46
[52] U.S. Cl. .................................. 204/1 T; 204/418; 204/435
[58] Field of Search ............... 204/416, 417, 418, 419, 204/435, 1 T

[56] References Cited

U.S. PATENT DOCUMENTS

| | | | |
|---|---|---|---|
| 4,171,246 | 10/1979 | Hamblen et al. | 204/1 T |
| 4,214,968 | 7/1980 | Battaglia et al. | 204/195 |
| 4,259,164 | 3/1981 | Rasch et al. | 204/195 |
| 4,263,343 | 4/1981 | Kim | 427/125 |
| 4,282,079 | 8/1981 | Chang et al. | 204/195 |
| 4,476,007 | 10/1984 | Toner et al. | 204/417 |
| 4,505,800 | 3/1985 | Toner et al. | 204/418 |
| 4,571,293 | 2/1986 | Seshimoto et al. | 204/418 |
| 4,608,149 | 8/1986 | Daniel et al. | 204/418 |

FOREIGN PATENT DOCUMENTS 58-102146  6/1983  Japan.

*Primary Examiner*—T. Tung
*Attorney, Agent, or Firm*—J. Lanny Tucker

[57] ABSTRACT

An improved dry-operative ion-selective electrode for the determination of sodium ions in aqueous fluids includes a dried internal reference electrode, a dried reference layer and a sodium ion-selective membrane composed of a binder material. The reference layer contains a metal salt and a hydrophilic binder material, and is buffered to a pH of from about 4 to about 8 with a water-soluble, organic dicarboxylic acid. This electrode can be manufactured with significantly less waste and exhibits improved uniformity in performance.

15 Claims, 1 Drawing Figure

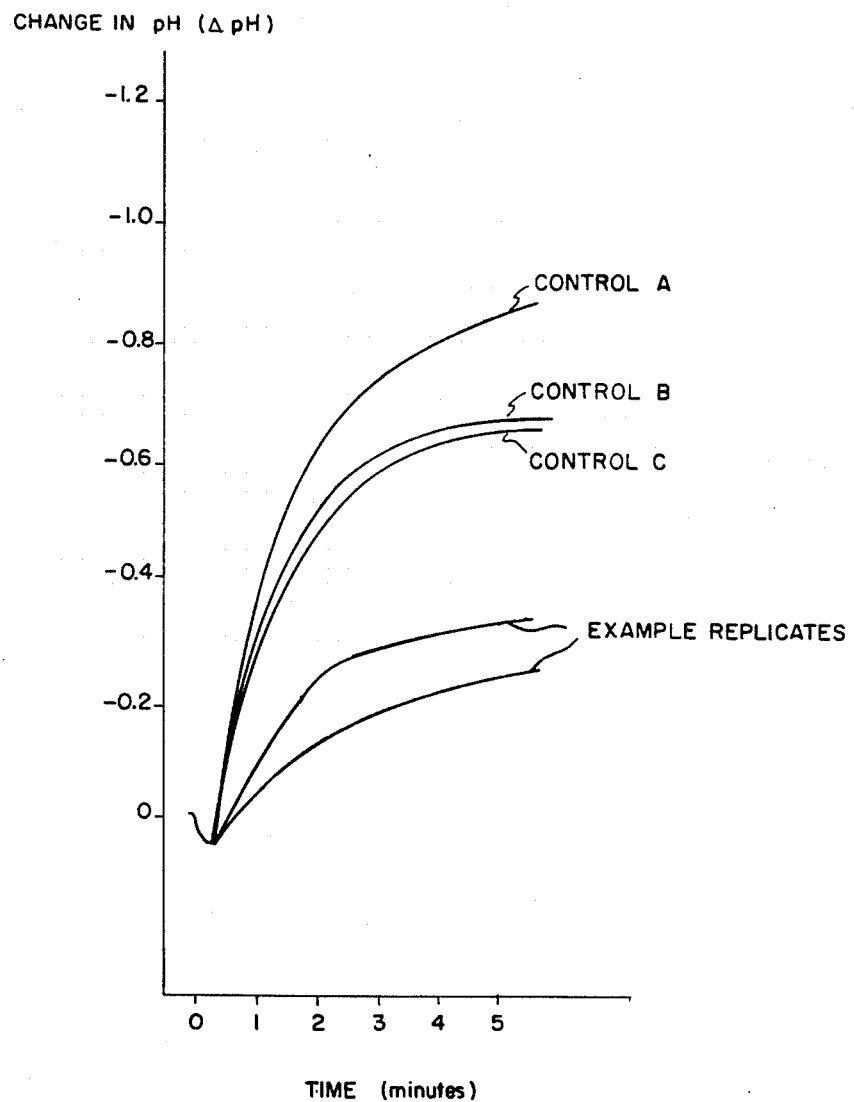

4,708,776

SODIUM ION SELECTIVE ELECTRODE AND METHOD OF USE

FIELD OF THE INVENTION

This invention relates to clinical chemistry and particularly to improved dry-operative sodium ion-selective electrodes and a method of use for the determination of sodium ions in aqueous fluids, e.g. biological fluids.

BACKGROUND OF THE INVENTION

In the diagnosis and treatment of various diseases as well as in preventative health care, it is important to monitor the concentrations of certain ions (e.g. cations) in a patient's body. One cation which has merited considerable attention in the diagnosis and treatment of heart disease, kidney disease and hypertension is sodium ion.

One type of electrode useful for determining the concentration of sodium ions in a fluid is generally composed of a reference electrode of some type and an ion-selective membrane. The reference electrode is a half-cell which contributes to providing a detectable potential during an assay. The ion-selective membrane can be made of glass or a polymeric binder material and is impregnated with an ion-selective carrier and a solvent for the carrier. The ion-sensitive carrier is also known as an ionophore and is a compound which is capable of sequentially complexing the desired ion (e.g. sodium), and transporting it across the membrane interface.

A significant advance in the art is the dry operative electrode described in U.S. Pat. No. 4,214,968 (issued July 29, 1980 to Battaglia et al). The electrodes described therein have the advantage of providing reproducible potentiometric determinations of ion activity with no requirement for wet storage or preconditioning prior to use. This patent describes the electrodes as having a dried electrolyte layer comprising a solid salt dispersed in a hydrophilic binder. This electrolyte layer is also known in the art as a reference layer.

U.S. Pat. No. 4,259,164 (issued Mar. 31, 1981 to Rasch et al) describes similar dry-operative ion-selective electrodes for the determination of potassium, carbonate and the like ions. These electrodes have an electrolyte layer which can comprise buffering agents, such as phosphates, acetic acid and the like (Col. 4, lines 40–55). Similar disclosures is provided in U.S. Pat. No. 4,263,343 (issued Apr. 21, 1981 to Kim) except that the inorganic compounds sodium hydroxide and hydrochloric acid are also mentioned as buffering agents. Neither reference teaches or suggests buffering the electrolyte layer at a pH of from about 4 to about 8 with a water-soluble, organic diacid.

Dry-operative sodium ion-selective electrodes like those described in U.S. Pat. No. 4,214,968, noted above, have been commercially available for some time in EKTACHEM Clinical Chemistry slides from Eastman Kodak Company (Rochester, N.Y. U.S.A.). While being a highly reliable and important diagnostic tool in the art, it has been difficult to efficiently manufacture slides exhibiting uniform assay performance. Generally, such slides are manufactured in a wide continuous web which is cut into strips having the proper width for individual slides. Uniformity in sodium determination among individual slides randomly selected from any location in a web is required for a viable commercial product. However, it has been observed that such uniformity is not always achieved without considerable waste. Reasons for the lack of performance uniformity among individual slides of a web are unknown. Because of this problem, considerable wasted product is generated at increased economic cost.

SUMMARY OF THE INVENTION

The problems noted above have been overcome with a dry-operative sodium ion-selective electrode comprising:

(a) a dried reference electrode in contact with (b) a dried reference layer buffered to a pH of from about 4 to 8 with a water soluble, organic dicarboxylic acid or salt thereof, which layer is in contact with one side of (c) an ion-selective membrane composition comprising an ionophore for sodium ions, a compound capable of solvating the ionophore and a supporting matrix comprising a binder material.

In a preferred embodiment described in more detail below, a dry-operative sodium ion selective electrode comprises a nonporous support having thereon:

(a) a dried silver/silver halide reference electrode in contact with (b) a dried reference layer comprising the dried residue of a water-soluble organic dicarboxylic acid or salt thereof which buffers the layer at a pH of from about 4 to about 8, a sodium salt and a hydrophilic binder material, which layer is in contact with one side of (c) an ion-selective membrane composition comprising an ester of monensin, a compound capable of solvating the ester and a hydrophobic binder material having carboxyl groups.

This invention also provides a method for potentiometrically determining sodium ions in an aqueous liquid comprising the steps of:

A. contacting a sample of a fluid suspected of containing sodium ions with the membrane of the electrode described above, B. connecting the electrode to a second reference electrode, and C. detecting and comparing the electrical potentials generated by sodium ions in contact with the electrodes.

The present invention provides a dry-operative electrode useful for the determination of sodium ions which can be manufactured more efficiently and reproducibly, thereby eliminating considerable waste. More particularly, the nonuniformity between individual strips of web used to prepare potentiometric slides is substantially reduced with this invention. These advantages are achieved by buffering the reference layer (sometimes called the electrolyte layer) at a pH of from about 4 to about 8 with a water-soluble, organic dicarboxylic acid or salt thereof. The presence of other buffers, e.g. phosphate or citric acid does not provide the same results (see the Examples below).

BRIEF DESCRIPTION OF THE DRAWINGS

The FIGURE contains graphical plots of the change in pH over time for compared reference layers as described in Example 2 below.

DETAILED DESCRIPTION OF THE INVENTION

In general, the electrodes of the present invention are prepared using components and methods described in detail in U.S. Pat. No. 4,214,968, noted above, the disclosure of which is incorporated herein in its entirety. Since most of the details are disclosed in that patent, the present disclosure will be directed to general summaries of the electrode components. As used herein, the terms "dry-operative" and "dried" have the meanings defined in U.S. Pat. No. 4,214,968.

The electrodes can also be constructed according to the teachings of Japanese Patent Publications Nos. 57(1982)-017851 and 57(1982)-017852.

The electrodes and devices of this invention can be used to determine the concentration of sodium ions in any aqueous liquid, including wastewater, cooling water, groundwater, food and brewery processing fluids, and the like. They are particularly useful for the assay of biological fluids, e.g. blood sera and urine.

The electrode of the present invention comprises an internal reference electrode which exhibits a reproducible reference potential against which the potential occurring at the interface between the ion-selective electrode and the solution under test is measured.

Generally, the reference electrode comprises a conductive metal layer of a suitable conductive metal (e.g. silver, mercury, platinum, nickel and the like). The conductive layer is in contact with a metal salt layer which may comprise substantially any insoluble salt of the metal in the conductive layer which establishes a fixed interfacial potential with the metal of the conductive layer. Preferably, the metal salt layer comprises a salt of the metal which is a product of oxidation of the metal, e.g. a silver halide, mercury halide, etc. Such layers and techniques for making them are well known and described in more detail in U.S. Pat. No. 4,214,968, noted above. Useful metal/metal salt electrodes include silver/silver halide and mercury/mercury chloride electrodes. Other useful reference electrodes are known in the art. A silver/silver halide reference electrode is preferred in the practice of this invention.

The sodium ion-selective electrodes of this invention also comprise a dried electrolyte or reference layer in contact with the reference electrode. In one embodiment, the dried reference layer contains the dried residue of a salt and a buffer (described below) and any optional addenda, but is binderless (e.g. according to U.S. Pat. No. 4,571,293, issued Feb. 18, 1986 to Seshimoto et al).

According to a preferred embodiment, the reference layer is a dried hydrophilic layer comprising one or more dried hydrophilic binder materials, a suitable buffer (described below) and a salt uniformly distributed in the binder materials. Preferrably, the anion of the salt is common to the salt of the metal salt layer of the reference electrode, and at least a portion of the cation of the salt is sodium. In this embodiment, the dried reference layer is the dried residue of a solution of the salt, the buffer and a suitable hydrophilic binder material (either natural or synthetic) in a solvent for the binder material and salt. The amounts and types of each component of the dried reference layer and the methods of preparation are readily determined by a skilled worker in the art in view of the teachings of U.S. Pat. No. 4,214,968 noted above, and Japanese Patent Publication No. 58(1983)-102146.

It is essential to the practice of this invention that the reference layer also comprise one or more water-soluble, organic dicarboxylic acids which buffer the layer to a pH of from about 4 to about 8. Preferably, the layer is buffered to a pH of from about 4.5 to about 6.5. Such organic diacids comprise two carboxyl groups attached to an organic backbone which can be saturated or unsaturated. For example, the acidic groups can be attached to aliphatic, alicyclic, aromatic and heterocyclic groups as long as the resulting compound is water-soluble. Generally, the compound has from 3 to 8 carbon atoms and suitable pKa to provide the desired buffering effect. Representative dicarboxylic acids include maleic acid, malic acid, malonic acid, glutaric acid, dimethylglutaric acid, glutaconic acid, succinic acid, suberic acid, phthalic acid and the like. The buffering compounds can be used as free acids or as salts thereof (alkali metal or ammonium). Preferred dicarboxylic acids are saturated or unsaturated and have from 3 to 6 carbon atoms. Succinic acid is most preferred in practicing this invention. Generally, the dicarboxylic acid is present in an amount of at least about 0.2 g/m$^2$, and preferably from about 0.5 to about 3 g/m$^2$ in the dried reference layer.

The dried reference layer is in contact with a sodium-ion selective membrane composition. This composition is laminated, coated or otherwise applied directly over the reference layer.

A variety of sodium-ion selective membrane compositions can be used in the practice of the present invention, including those described in U.S. Pat. No. 4,214,968 and references noted therein. Generally, the composition comprises an ionophore for sodium ions, a compound capable of solvating the ionophore and a supporting matrix comprised of one or more binder materials. The matrix can be any material which is capable of forming a thin film of sufficient permeability to produce, in combination with the ionophore and solvent, sodium ion mobility thereacross. Useful materials include porous glass, pressed fibers, and synthetic and natural polymeric materials, such as poly(vinyl chloride), carboxylated poly(vinyl chloride), poly(styrene-co-styrene sulfonic acid), poly(vinyl chloride-co-styrene sulfonic acid), poly(vinyl chloride-co-styrene carboxylic acid) and the like. Poly(vinyl chloride) is a preferred binder material in the practice of this invention.

Useful ionophores include hemispherands, such as those described in European Patent Application No. 111,817, U.S. Pat. No. 4,476,007 (issued Oct. 9, 1984 to Toner et al) and 4,505,800 (issued Mar. 19, 1985 to Toner et al), crown ethers, such as those described in U.S. Pat. No. 4,504,368 (issued Mar. 12, 1985 to Delton et al), monensin and esters thereof (e.g. methyl monensin), and others known in the art as described in U.S. Pat. No. 4,214,968, noted above. Preferred ionophores are hemispherands, crown ethers and esters of monensin, with esters of monensin being more preferred and methyl monensin most preferred.

The ionophore is solvated by one or more organic solvents which are capable of at least partially solvating the ionophore and providing sodium ion mobility. If a hydrophobic binder is used as the supporting matrix, the solvent must be compatible with the binder. The solvent is sometimes identified in the art as a carrier solvent. Useful solvents include phthalates, sebacates, aromatic and aliphatic ethers, phosphates, mixed aromatic aliphatic phosphonates, adipates, nitrated ethers or esters or mixtures thereof, and others known in the art.

Membranes including hydrophobic binder materials, an ionophore and solvating solvents are prepared using known film-coating or casting techniques. The amounts of each membrane component, including optional addenda, are readily determined from the disclosures of the references noted above.

The electrodes of this invention can be self-supporting, meaning that one or more layers of the electrode have sufficient mechanical strength to support the remaining portions of the electrode. Preferably, however, they further include a support which may be comprised of any material capable of bearing, either directly or by virtue of some intervening adhesion-improving layer, the other necessary portions of the electrode described herein. The support may be porous or nonporous and be composed of wood, cellulose, ceramic, metal, glass, filter paper, polymeric or glass fibers, polymeric films and the like. Preferably, the support is prepared from a nonporous polymeric film.

Sodium ion activity can be measured with the electrode of the present invention by measuring the steady-state difference in electrical potential between the fluid to be tested (test fluid) and a reference fluid in a cell arrangement schematically represented by the following:

Reference electrode 1/test fluid/membrane/reference fluid/reference electrode 2. The calculations required to determine the ionic activity of the test fluid are derived from the well-known Nernst equation and are known to a skilled worker in the art.

The electrode of this invention incorporates within its structure substantially all of the components needed for making a potentiometric determination with the exception of a second reference electrode, a potential-indicating device (e.g. an electrometer or potentiometer) and associated wiring. In use, the user merely contacts the membrane of the electrode with a sample of the test fluid (e.g. less than 200 $\mu$l) and connects the electrodes to a potential-indicating device. Contacting the fluid with the membrane can be done in any suitable manner, but preferably, a sample of the test fluid is "spotted" onto the membrane with a suitable dispensing means. Second reference electrodes for use in the assay, such as standard calomel electrodes, are well known. Similarly, electrometers are well known.

Alternatively and preferably, two or more electrodes of the present invention are incorporated or mounted into a frame to form a single device, slide or "chip" as it is sometimes known in the art. One of the electrodes is used to contact the test fluid while another is used as the second reference electrode to which the reference solution is connected Such a device is described in more detail in U.S. Pat. No. 4,171,246, (issued Oct. 16, 1979 to Hamblen et al). Such devices generally comprise a means for providing a liquid junction between the electrodes, including a capillary bridge formed of a strip of paper, a standard chromatographic strip, a strip of a porous polymeric film, natural or synthetic threads or fibers, etc. Reference fluids useful in practicing the present invention are known in the art and commercially available.

In the examples which follow illustrating the practice of the invention, the materials used in constructing the electrode were obtained as follows:

DC-510 polysilicone surfactant from Dow Corning (Midland, Mich. U.S.A.), SURFACTANT 10G nonionic surfactant from Olin Corporation (Stamford, Connecticut, U.S.A.), and the remainder from Eastman Kodak Co. (Rochester, New York, U.S.A.) or prepared using standard starting materials and known procedures.

EXAMPLE 1

Dry-Operative Sodium Ion-Selective Electrode and Sodium Assay

This is a comparative example showing the improvement in performance uniformity obtained with the present invention as compared to electrodes of the prior art.

A dry-operative sodium-ion selective electrode of the present invention was prepared having the following format and components according to the procedures described in U.S. Pat. No. 4,214,968, noted above:

| | | |
|---|---|---|
| Membrane | Poly(vinyl chloride) (1.8% carboxylated) | 3–15 g/m$^2$ |
| | Bis(2-ethylhexyl) sebacate | 4–20 g/m$^2$ |
| | Methyl monensin | 0.2–1 g/m$^2$ |
| | DC-510 TM silicone surfactant | 0.005–0.1 g/m$^2$ |
| Reference Layer (pH 5.5) | Gelatin | 3–12 g/m$^2$ |
| | Sodium chloride | 0.5–8 g/m$^2$ |
| | Glycerol | 0.1–1 g/m$^2$ |
| | Biocide | 0.005–0.1 g/m$^2$ |
| | SURFACTANT 10G nonionic surfactant | 0.001–0.1 g/m$^2$ |
| | Succinic acid (pH 5.5) | 0.2–3 g/m$^2$ |
| Reference Electrode | Silver chloride | 0.1–3 g/m$^2$ |
| | Silver | 0.5–10 g/m$^2$ |

Three Control electrodes were similarly prepared with the following differences: Control A contained no succinic acid in the Reference Layer, Control B contained citric acid (pH 5.5) in place of the succinic acid, and Control C contained phosphoric acid (pH 5.5) in place of the succinic acid. The pH of the reference layer in each electrode was adjusted to the desired value using sodium hydroxide.

These electrodes are prepared from individual continuous webs in manufacturing operations which were up to about 30 cm in width. Each of the webs from which the electrodes were prepared were tested for uniformity in performance across its full width. This was done by randomly selecting individual electrodes prepared from two different locations in the webs and spotting them with 10 $\mu$l samples of a reconstituted bovine serum albumin based lyophilate containing various amounts of sodium ions (90–210 milliequivalents/liter) onto the membranes of the electrodes. Some electrodes were tested immediately after manufacture (fresh). All of the electrodes were tested after 2 weeks of storage at 21° C. and 50% relative humidity (aged).

Sodium ion concentration was then measured in each test using a standard EKTACHEM Clinical Chemistry Analyzer and standard calculations using a calibration curve.

The results of predicted sodium ion concentrations (meq/l) at the two different locations and the difference ($\Delta$meq/l) for each electrode are shown in Table 1 below. It is apparent from the data that the electrode of the present invention shows significantly improved uniformity in performance as compared to the Control electrodes. Generally, a difference in predicted values of less than about 1% is desirable.

TABLE I

| Elec-trode | Fresh Tests (meq/l) | | | Aged Tests (meq/l) | | |
|---|---|---|---|---|---|---|
|  | Test 1 | Test 2 | Δ meq/l | Test 1 | Test 2 | Δ·meq/l |
| Example 1 | 134.35 | 134.56 | 0.21 | 108.39 | 108.27 | 0.12 |
| Control A | NA | NA |  | 132.18 | 121.34 | 10.84 |
| Control B | NA | NA |  | 127.19 | 132.29 | 5.10 |
| Control C | 148.76 | 150.87 | 2.11 | 126.81 | 128.95 | 2.14 |

NA = Test not conducted and data not available.

EXAMPLE 2

This is a comparative example illustrating the difference in acid released from the compared electrodes shown in Example 1 after the electrodes were spotted with a drop of an aqueous solution of sodium chloride (0.1 molar). The pH measurements used to determine acid release were made by placing a flat combination pH electrode into the drop of fluid. The Controls are the same as those identified in that example.

The FIGURE shows the amount of acid released from the compared electrodes having reference layers containing the different buffers over several minutes. Two replicates were made for each electrode reference layer, but the replicates of each Control layer were indistinguishable. It can be seen that the electrode of the present invention released significantly less acid than the Control electrodes. While the mechanism for the improvements obtained with this invention are unknown, it is believed that the acid released from an electrode which is not neturalized in some manner may contribute to the non-uniformity observed in manufactured electrodes of the art.

The invention has been described in detail with particular reference to preferred embodiments thereof, but it will be understood that variations and modifications can be effected within the spirit and scope of the invention.

We claim:

1. A dry-operative sodium ion-selective electrode comprising:
   (a) a dried reference electrode in contact with
   (b) a dried reference layer buffered to a pH of from about 4 to about 8 with a water-soluble, organic dicarboxylic acid or salt thereof, which layer is in contact with one side of
   (c) an ion-selective membrane composition comprising an ionophore for sodium ions, a compound capable of solvating said ionophore and a supporting matrix composed of a binder material.

2. The electrode of claim 1 wherein said reference layer comprises at least one metal salt distributed in a hydrophilic binder material.

3. The electrode of claim 2 wherein said metal salt is a sodium salt.

4. The electrode of claim 1 wherein said supporting matrix is a hydrophobic polymeric binder material.

5. The electrode of claim 1 wherein said solvating compound is selected from the group consisting of phthalates, sebacates, aromatic and aliphatic ethers, phosphates, mixed aromatic aliphatic phosphonates, adipates, nitrated ethers or esters, and mixtures thereof.

6. The electrode of claim 1 wherein said ionophore is selected from the group consisting of hemispherands, crown ethers, monensin and esters thereof.

7. The electrode of claim 1 further comprising a support, said reference electrode being disposed between said support and said membrane.

8. The electrode of claim 1 wherein said reference electrode is a silver/silver halide reference electrode.

9. A dry operative sodium ion-selective electrode comprising a nonporous support having thereon;
   (a) a silver/silver halide reference electrode in contact with
   (b) a dried reference·layer comprising the dried residue of a water-soluble organic dicarboxylic acid or salt thereof which buffers said layer at a pH of from about 4 to about 8, a sodium salt and a hydrophilic binder material, which layer is in contact with one side of
   (c) an ion-selective membrane composition comprising an ester of monensin, a compound capable of solvating said ester and a hydrophobic polymeric binder material.

10. The electrode of claim 9 wherein said ionophore is methyl monensin, said hydrophobic polymeric binder material is poly(vinyl chloride), said hydrophilic binder material is carboxylated poly(vinyl chloride), and said dicarboxylic acid is maleic acid, malic acid, malonic acid, glutaric acid, dimethylglutaric acid, glutaconic acid, succinic acid, suberic acid, phthalic acid or an equivalent salt thereof.

11. The electrode of claim 9 wherein said dicarboxylic acid is succinic acid.

12. The electrode of claim 9 wherein said dicarboxylic acid is present in an amount of at least about 0.2 $g/m^2$.

13. A method for potentiometrically determining sodium ions in an aqueous liquid comprising the steps of:
   A. contacting a sample of a fluid suspected of containing sodium ions with the membrane of the electrode of claim 1,
   B. connecting said electrode to a second reference electrode, and
   C. detecting and comparing the electrical potentials generated by sodium ions in contact with said electrodes.

14. The method of claim 13 wherein both of said electrodes are mounted in a frame of a single device comprising a means for transporting sodium ions between said electrodes, and said second reference electrode is contacted with a sample of a reference fluid containing a known amount of sodium ions.

15. The method of claim 13 wherein said detecting and comparing step comprises connecting an electrometer to said electrodes, whereby said electrometer displays the difference in said potentials.

* * * * *